(12) United States Patent　　(10) Patent No.:　　US 9,375,419 B1
Suto　　　　　　　　　　　　　　(45) Date of Patent:　　Jun. 28, 2016

(54) ANTIVIRAL AGENTS

(71) Applicant: Southern Research Institute, Birmingham, AL (US)

(72) Inventor: Mark J. Suto, Birmingham, AL (US)

(73) Assignee: Southern Research Institute, Birmingham, AL (US)

( * ) Notice: Subject to any disclaimer, the term of this patent is extended or adjusted under 35 U.S.C. 154(b) by 0 days.

(21) Appl. No.: 14/962,197

(22) Filed: Dec. 8, 2015

Related U.S. Application Data

(60) Provisional application No. 62/089,933, filed on Dec. 10, 2014.

(51) Int. Cl.
　　*A61K 31/435*　　(2006.01)
　　*A61K 31/4439*　　(2006.01)
(52) U.S. Cl.
　　CPC ........... *A61K 31/4439* (2013.01); *A61K 31/435* (2013.01)
(58) Field of Classification Search
　　None
　　See application file for complete search history.

*Primary Examiner* — Yevegeny Valenrod
(74) *Attorney, Agent, or Firm* — Polsinelli PC

(57) ABSTRACT

A method for treating or preventing a norovirus, such as Norwalk virus, infection in a subject, which comprises administering to said subject in need thereof a therapeutically effective amount of at least one compound selected from the group consisting of:

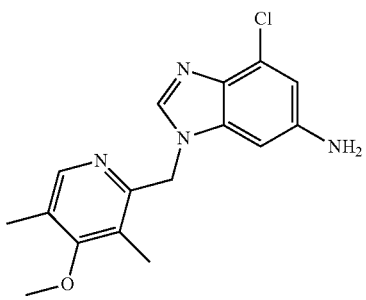

Compound 1

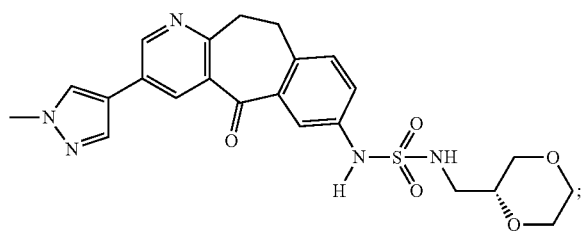

Compound 2 a pharmaceutically acceptable salt thereof or solvate thereof or mixtures thereof. The subject can be an animal, particularly mammals and more particularly humans and companion animals such as cats and dogs.

19 Claims, No Drawings

ANTIVIRAL AGENTS

CROSS REFERENCE TO RELATED APPLICATION

This application claims priority under 35 U.S.C. §119(e) to U.S. Provisional Application No. 62/089,933 filed on Dec. 10, 2014, the entire contents of which are hereby incorporated by reference.

TECHNICAL FIELD

The present disclosure relates to treating or preventing viral infection from Norovirus by administering a therapeutically effective amount of a compound, pharmaceutically acceptable salt thereof or solvate thereof.

BACKGROUND OF DISCLOSURE

Norovirus is a very contagious virus. You can get a norovirus infection from an infected person, contaminated food or water, or by touching contaminated surfaces. The virus causes your stomach or intestines or both to become inflamed (acute gastroenteritis) leading to stomach pain, nausea, and diarrhea.

Anyone can be infected with Norovirus. Also, you can become infected many times in your life and can be serious, especially for young children and older adults.

Norovirus is the most common cause of acute gastroenteritis in the United States. Each year, it causes 19-21 million illnesses and contributes to 56,000-71,000 hospitalizations and 570-800 deaths. Norovirus is also the most common cause of foodborne-disease outbreaks in the United States.

SUMMARY OF DISCLOSURE

The present disclosure relates to treating or preventing viral infection from certain viral infections, and in particular, Norovirus by administering to a subject in need thereof a therapeutically effective amount of Compound 1 or Compound 2, identified below, or a pharmaceutically acceptable salt thereof or solvate thereof. The virus treated according to this disclosure includes Norovirus. The subjects treated include animals, particularly mammals and more particularly humans and companion animals such as cats and dogs.

According to the present disclosure, a therapeutically effective amount of at least one compound selected from the group consisting of Compound 1 or Compound 2 is administered to a subject in need thereof:

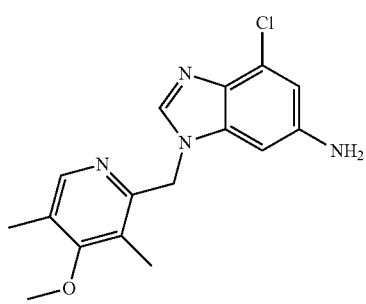
Compound 1

4-Chloro-1-((4-methoxy-3,5-dimethylpyridin-2-yl)methyl)-1H-benzo[d]imidazo-6-amine

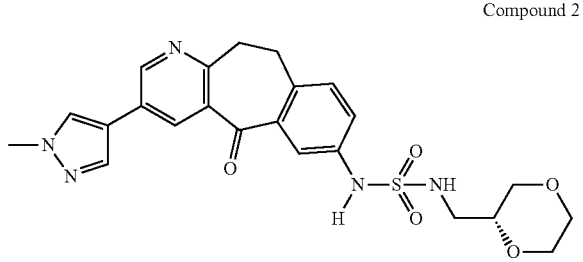 [SMILES: Cn1cc(-c2cnc3c(c2)C(=O)c2cc(NS(=O)(=O)NC[C@@H]4COCCO4)ccc2CC3)cn1]
Compound 2

N-((2R)-1,4-Dioxan-2-ylmethyl)-N-methyl-N'-[3-(1-methyl-1H-pyrazol-4-yl)-5-oxo-5H-benzo[4,5]cyclohepta[1,2-b]pyridin-7-yl]sulfamide;
a pharmaceutically acceptable salt thereof or solvate thereof or mixtures thereof.

BEST AND VARIOUS MODES FOR CARRYING OUT DISCLOSURE

The present disclosure is concerned with a process for treating or preventing a viral infection in a subject, wherein the viral infection is from Norovirus, such as Norwalk virus. The process comprises administering to the subject in need thereof a therapeutically effective amount of at least one compound represented by the formulae:

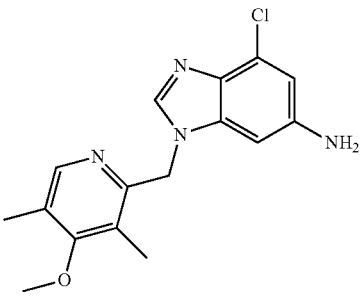
Compound 1

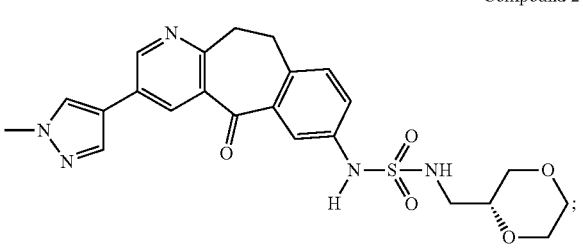
Compound 2 a pharmaceutically acceptable salt thereof or solvate thereof or mixtures thereof.

It is of course understood that the compounds of the present disclosure relate to all optical isomers and stereo-isomers at the various possible atoms of the molecule, unless specified otherwise.

"Pharmaceutically acceptable salts" refer to derivatives of the disclosed compounds wherein the parent compound is modified by making acid or base salts thereof. The compounds of this disclosure form acid and base addition salts with a wide variety of organic and inorganic acids and bases and includes the physiologically acceptable salts which are often used in pharmaceutical chemistry. Such salts are also part of this disclosure. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkonic acids, hydroxyalkanoic and hydroxyalkandioic acids, aromatic acids, aliphatic and aromatic sulfonic acids may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, O-hydroxybutyrate, butyne-1,4-dioate, hexyne-1,4-dioate, cabrate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toleunesulfonate, xylenesulfonate, tartarate, and the like.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include sodium hydroxide, potassium hydroxide, ammonium hydroxide, potassium carbonate, methylamine, diethylamine, and ethylene diamine.

"Solvates" refer to the compound formed by the interaction of a solvent and a solute and includes hydrates. Solvates are usually crystalline solid adducts containing solvent molecules within the crystal structure, in either stoichiometric or non-stoichiometric proportions.

The terms "effective amount" or "therapeutically effective amount" refer to an amount of the compound of the disclosure sufficient to provide a benefit in the treatment or prevention of viral disease, to delay or minimize symptoms associated with viral infection or viral-induced disease, or to cure or ameliorate the disease or infection or cause thereof. In particular, a therapeutically effective amount means an amount sufficient to provide a therapeutic benefit in vivo. Used in connection with an amount of a compound of the disclosure, the term preferably encompasses a non-toxic amount that improves overall therapy, reduces or avoids symptoms or causes of disease, or enhances the therapeutic efficacy of or synergies with another therapeutic agent.

The term "treating" refers to relieving the disease, disorder, or condition, i.e., causing regression of the disease, disorder, and/or condition. The term "preventing" refers to preventing a disease, disorder, or condition from occurring in a human or an animal that may be predisposed to the disease, disorder and/or condition, but has not yet been diagnosed as having it; and/or inhibiting the disease, disorder, or condition, i.e arresting its development.

The compounds employed according to the present disclosure are readily available commercially and therefore a discussion of their preparation is not necessary.

It was surprisingly found according to the present disclosure that the above compounds are active against Norovirus. Compounds 1 and 2 were found to be active in the primary screen and the data confirmed in the secondary assay, as disclosed below. However, they did not have activity in any of the other viruses tested, which include Herpes Simpex Virus 1 and 2, Human cytomegalovirus, Yellow fever virus, Rift valley fever virus, tacaribe virus, polio virus, Venezuelan equine encephalalitis virus, Vaccina virus, Hepatitis B and C virus, and Adenorovirusirus-5.

Method of Testing:
Primary Anti-Norovirus Assay—In-Vitro Antiviral Screening RNA Hybridization (Replicon)

Antiviral activity against a human Norovirus (Norovirus) is assessed in a 3-day assay using the stably-expressing human Norovirus replicon cell line, HG23 (genogroup I, genomic length; parental cell line, HuH7) (Chang, et al., 2006, Virol. 353:463) maintained as sub-confluent cultures on 96-well plates. Typically, 4 doses (10-fold or 3-fold steps), in triplicate are used. Antiviral activity is determined by blot hybridization analysis of intracellular Norovirus RNA (normalized to the level of cellular $\beta$-actin RNA in each culture sample). Cytotoxicity is assessed by neutral red dye uptake in cultures maintained in parallel plates (Korba and Gerin, 1992, Antivir. Res. 19:55).

$EC_{50}$, $EC_{90}$ and $CC_{50}$ values are calculated by linear regression analysis (MS EXCEL®, QuattroPro®) using data combined from all treated cultures (Korba & Gerin, 1992, Antivir. Res. 19:55; Okuse, et al., 2005, Antivir. Res. 65:23). Standard deviations for $EC_{50}$ and $EC_{90}$ values are calculated from the standard errors generated by the regression analyses. $EC_{50}$ and $EC_{90}$ are drug concentrations at which a 2-fold, or a 10-fold depression of intracellular Norovirus RNA (relative to the average levels in untreated cultures), respectively, is observed. $CC_{50}$ is the drug concentration at which a 2-fold lower level of neutral red dye uptake (relative to the average levels in untreated cultures) is observed. The Selectivity index (S.I.) is calculated as $CC_{50}/EC_{50}$. Recombinant human interferon 2b (PBL laboratories, Inc.) is used as an assay control.
Secondary Anti-Norvirus Assay—Quantitative Polymerase Chain Reaction
(Replicon)/Neutral Red (Toxicity)

The secondary anti-Norovirus assay is conducted as described for the primary assay above. Norovirus RNA is quantified using a real time PCR method (Chang, et al., 2006, Virol. 353:463), normalized to the level of cellular $\beta$-actin RNA in each culture sample.

| In-Vitro Antiviral Screening RNA Hybridization (Replicon) | | | | | |
| --- | --- | --- | --- | --- | --- |
| Virus Screened: | | Norvirus | | | |
| Virus Stain: | | $GT_1$ | | | |
| Cell Line: | | $HG_{23}$ | | | |
| Vehicle: | | DMSO | | | |
| Drug Conc. Range: | | 0.1-100 $\mu$M | | | |
| Control Conc. Range: | | 1.1-300 $\mu$M | | | |
| Control Drug Name | $EC_{50}$ | $EC_{90}$ | $CC_{50}$ | $SI_{50}$ | $SI_{90}$ |
| 2'C-methyl cytidine | 6.2 | 19 | 300 | >48 | >16 |
| Compound 1 | 0.617 | 7.5 | >100 | >162 | >13 |
| Compound 2 | 0.331 | 0.986 | 35 | 106 | 35 |

$EC_{50}$ - compound concentration that reduces viral replication by 50%
$EC_{90}$ - compound concentration that reduces viral replication by 90%
$CC_{50}$ - compound concentration that reduces cell viability by 50%
$SI_{50}$ - $CC_{50}/EC_{50}$
$SI_{90}$ - $CC_{50}/EC_{90}$

| Quantitative Polymerase Chain Reaction (Replicon)/Neutral Red (Toxicity) | | | | | |
|---|---|---|---|---|---|
| Virus Screened | NOROVIRUS | | | | |
| Virus Stain: | $GT_1$ | | | | |
| Cell Line: | $HG_{23}$ | | | | |
| Vehicle: | DMSO | | | | |
| Drug Conc. Rang | 0.1-500 □M | | | | |
| Control Conc. Range: | 1.1-300 □M | | | | |
| Control Drug Name | $EC_{50}$ | $EC_{90}$ | $CC_{50}$ | $SI_{50}$ | $SI_{90}$ |
| 2'C-methyl cytidine | 6.0 | 18 | >300 | >50 | >17 |
| Compound 1 | 1.4 | 8.5 | >50 | >36 | >6 |
| Compound 2 | 0.641 | 1.4 | 28 | 44 | 20 |

$EC_{50}$ - compound concentration that reduces viral replication by 50%
$EC_{90}$ - compound concentration that reduces viral replication by 90%
$CC_{50}$ - compound concentration that reduces cell viability by 50%
$SI_{50}$ - $CC_{50}/EC_{50}$
$SI_{90}$ - $CC_{50}/EC_{90}$ Exemplary embodiments according to the present disclosure are;

Embodiment 1

A method for treating or preventing a Norovirus infection in a subject, which comprises administering to said subject in need thereof a therapeutically effective amount of at least one compound selected from the group consisting of:

Compound 1

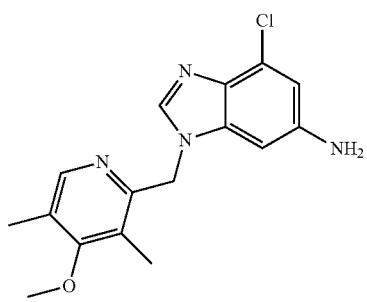 [SMILES: COc1c(C)cnc(Cn2cnc3c(Cl)cc(N)cc32)c1C]

Compound 2

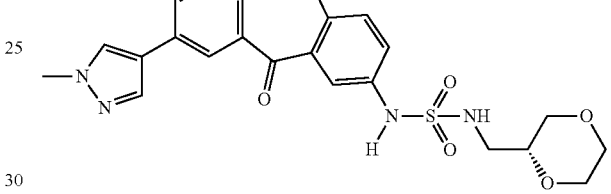

a pharmaceutically acceptable salt thereof or solvate thereof or mixtures thereof.

Embodiment 2

The method according to Embodiment 1, wherein said compound is

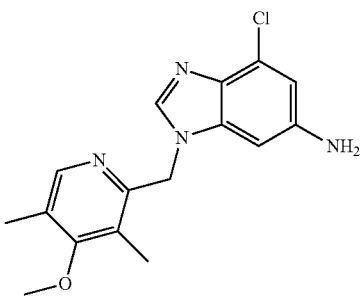 [SMILES: COc1c(C)cnc(Cn2cnc3c(Cl)cc(N)cc32)c1C]

a pharmaceutically acceptable salt thereof or solvate thereof.

Embodiment 3

The method according to Embodiment 1, wherein said compound is:

a pharmaceutically acceptable salt thereof or solvate thereof.

Embodiment 4

The method according to any one of Embodiments 1, 2 or 3, wherein said subject is an animal.

Embodiment 5

The method according to any one of Embodiments 1, 2 or 3, wherein said subject is a human.

Embodiment 6

The method according to any one of claim 1, 2 or 3, wherein said subject is a companion animal.

Embodiment 7

The method according to any one of Embodiments 1, 2, 3, 4, 5 or 6 wherein said Norovirus is Norwalk virus.

The compounds of the present disclosure can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice. The compounds can also be administered in conjunction with other therapeutic agents.

The pharmaceutically acceptable carriers described herein, for example, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The compounds of this disclosure can be administered by any conventional method available for use in conjunction with pharmaceuticals, either as individual therapeutic agents or in a combination of therapeutic agents.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to 1000 milligrams (mg) per kilogram (kg) of body weight, with the preferred dose being 0.1 to about 30 mg/kg.

Dosage forms (compositions suitable for administration) typically contain from about 1 mg to about 500 mg of active ingredient per unit. In these pharmaceutical compositions, the active ingredient will ordinarily be present in an amount of about 0.5-95% weight based on the total weight of the composition.

The active ingredient can be administered orally in solid dosage forms, such as capsules, tablets, and powders, or in liquid dosage forms, such as elixirs, syrups and suspensions. It can also be administered parenterally, in sterile liquid dosage forms. The active ingredient can also be administered intranasally (nose drops) or by inhalation of a drug powder mist. Other dosage forms are potentially possible such as administration transdermally, via patch mechanism or ointment.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition.

Accordingly, there is a wide variety of suitable formulations of the pharmaceutical composition of the present disclosure. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, Eds., 238-250 (1982) and *ASHP Handbook on Injectable Drugs*, Toissel, 4th ed., 622-630 (1986).

Suitable pharmaceutical carriers are described in Remington's Pharmaceutical Sciences, Mack Publishing Company, a standard reference text in this field.

The dose administered to an animal, particularly a human, in the context of the present disclosure should be sufficient to affect a therapeutic response in the animal over a reasonable time frame. One skilled in the art will recognize that dosage will depend upon a variety of factors including a condition of the animal, the body weight of the animal, as well as the severity and stage of the condition being treated.

A suitable dose is that which will result in a concentration of the active agent in a patient which is known to affect the desired response. The preferred dosage is the amount which results in maximum inhibition of the condition being treated, without unmanageable side effects.

The size of the dose also will be determined by the route, timing and frequency of administration as well as the existence, nature, and extend of any adverse side effects that might accompany the administration of the compound and the desired physiological effect.

Useful pharmaceutical dosage forms for administration of the compounds according to the present disclosure can be illustrated as follows:

Hard Shell Capsules

A large number of unit capsules are prepared by filling standard two-piece hard gelatine capsules each with 100 mg of powdered active ingredient, 150 mg of lactose, 50 mg of cellulose and 6 mg of magnesium stearate.

Soft Gelatin Capsules

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets

A large number of tablets are prepared by conventional procedures so that the dosage unit was 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules

These are solid oral dosage forms made by conventional and norovirusel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All publications, patents and patent applications cited in this specification are herein incorporated by reference, and for any and all purpose, as if each individual publication, patent or patent application were specifically and individually indicated to be incorporated by reference. In the case of inconsistencies, the present disclosure will prevail.

The foregoing description of the disclosure illustrates and describes the present disclosure. Additionally, the disclosure shows and describes only the preferred embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The embodiments described hereinabove are further intended to explain best modes known of practicing it and to enable others skilled in the art to utilize the disclosure in such, or other, embodiments and with the various modifications required by the particular applications or uses. Accordingly, the description is not intended to limit it to the form disclosed herein. Also, it is intended that the appended claims be construed to include alternative embodiments.

What is claimed is:

1. A method for treating a Norovirus infection in a subject or treating a subject who has been exposed to the Norovirus but has not yet been diagnosed as being infected, which comprises administering to the subject in need thereof a therapeutically effective amount of at least one compound selected from the group consisting of:

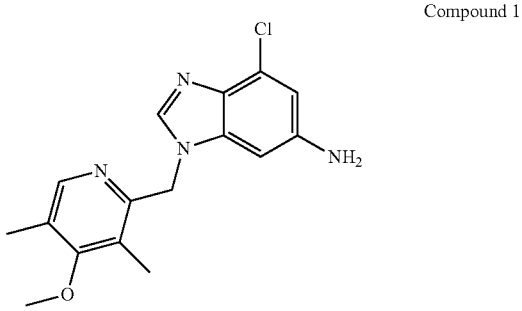

Compound 1

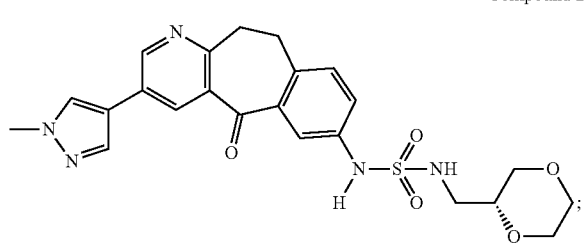

Compound 2 a pharmaceutically acceptable salt thereof or solvate thereof or mixtures thereof.

2. The method according to claim 1, wherein said compound is

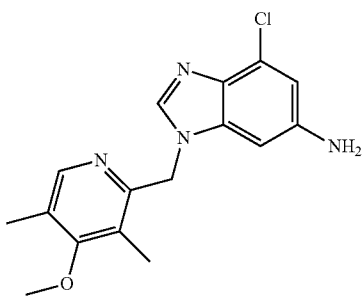

a pharmaceutically acceptable salt thereof or solvate thereof.

3. The method according to claim 1, wherein said compound is:

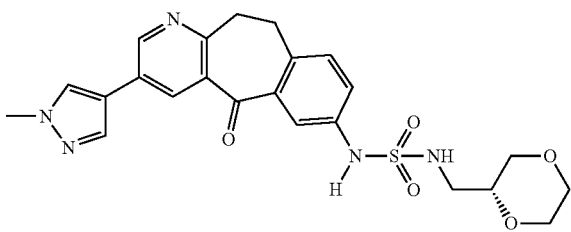 [SMILES: Cn1cc(-c2cnc3c(c2)C(=O)c2cc(NS(=O)(=O)NC[C@@H]4COCCO4)ccc2CC3)cn1]

a pharmaceutically acceptable salt thereof or solvate thereof.

4. The method according to claim 1 wherein said Norovirus is Norwalk virus.

5. The method according to claim 2 wherein said Norovirus is Norwalk virus.

6. The method according to claim 3 wherein said Norovirus is Norwalk virus.

7. The method according to 1, wherein said subject is an animal.

8. The method according to 2, wherein said subject is an animal.

9. The method according to 3, wherein said subject is an animal.

10. The method according to 4, wherein said subject is an animal.

11. The method according to 5, wherein said subject is an animal.

12. The method according to 6, wherein said subject is an animal.

13. The method according to claim 1, wherein said subject is a human.

14. The method according to claim 2, wherein said subject is a human.

15. The method according to claim 3, wherein said subject is a human.

16. The method according to claim 4, wherein said subject is a human.

17. The method according to claim 5, wherein said subject is a human.

18. The method according to claim 6, wherein said subject is a human.

19. The method according to claim 1, wherein said subject is a companion animal.

* * * * *